United States Patent
Wang et al.

(10) Patent No.: US 6,638,587 B1
(45) Date of Patent: Oct. 28, 2003

(54) ELASTOMERIC ARTICLE HAVING SILICONE-BASED COMPOSITE COATING

(75) Inventors: Shiping Wang, Libertyville, IL (US); Yun-Siung Tony Yeh, Libertyville, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/552,479

(22) Filed: Apr. 18, 2000

(51) Int. Cl.[7] ............................................. B32B 25/08
(52) U.S. Cl. .................. 428/35.7; 428/36.8; 428/423.9; 428/424.2; 428/424.7; 428/424.8; 428/451; 524/506; 524/591
(58) Field of Search ............................. 428/35.7, 36.8, 428/423.9, 424.2, 424.7, 424.8; 224/506, 591

(56) References Cited

U.S. PATENT DOCUMENTS

| | | |
|---|---|---|
| 4,035,332 A | 7/1977 | Gomyo et al. ............... 260/33.2 |
| 4,070,713 A | 1/1978 | Stockum ........................ 2/168 |
| 4,199,648 A | 4/1980 | Curry et al. ................. 428/409 |
| 4,535,126 A | 8/1985 | Iida ............................ 525/106 |
| 4,742,142 A | 5/1988 | Shimuzu et al. .............. 528/15 |
| 4,962,165 A | 10/1990 | Bortnick et al. ............. 525/479 |
| 5,088,125 A | 2/1992 | Ansell et al. .................. 2/167 |
| 5,188,899 A | 2/1993 | Matsumoto et al. ......... 428/405 |
| 5,272,771 A | 12/1993 | Ansell et al. ................. 2/167 |
| 5,395,666 A | 3/1995 | Brindle ....................... 429/36.4 |
| 5,405,666 A | 4/1995 | Brindle ....................... 428/36.4 |
| 5,527,841 A * | 6/1996 | Inokuchi et al. ............ 523/435 |
| 5,534,350 A | 7/1996 | Liou ........................ 428/423.1 |
| 5,589,563 A | 12/1996 | Ward et al. .................... 528/44 |
| 5,700,585 A | 12/1997 | Lee ............................. 428/500 |
| 5,742,943 A | 4/1998 | Chen ............................. 2/168 |
| 5,777,052 A | 7/1998 | Kobayashi et al. ......... 526/279 |
| 5,792,531 A | 8/1998 | Littleton et al. ........... 428/36.8 |
| 5,969,022 A | 10/1999 | Bova et al. .................. 524/232 |
| 5,969,053 A | 10/1999 | Bauman et al. .......... 525/331.5 |
| 6,347,408 B1 * | 2/2002 | Yeh ............................... 2/167 |

FOREIGN PATENT DOCUMENTS

EP      0 822 232 A2    2/1998

\* cited by examiner

*Primary Examiner*—Sandra M. Nolan
(74) *Attorney, Agent, or Firm*—Andrew G. Rozycki

(57) ABSTRACT

The invention disclosed herein relates to an elastomeric article, such as a glove, containing an elastomeric material such as latex and a coating layer formed from an aqueous dispersion containing a composite of a silicone-modified polymer, e.g., a silicone-modified polyurethane, and silicone resin particles integrated therein. The interaction between the silicone groups on both the polymer and particles produces enhances binding effectiveness of the particles to the material. Gloves and other articles made in accordance with the invention contain a microroughened skin-contacting surface and exhibit a reduced coefficient of friction and increased lubricity, thereby enhancing the donning properties thereof.

39 Claims, 2 Drawing Sheets

ELASTOMERIC ARTICLE HAVING SILICONE-BASED COMPOSITE COATING

FIELD OF THE INVENTION

The invention relates to elastomeric articles used in medical applications. In particular, the invention pertains to elastomeric articles such as medical gloves having reduced coefficient of friction with respect to the skin-contacting surface.

BACKGROUND OF THE INVENTION

Surfaces of elastomeric articles generally exhibit poor lubricity when contacting a dry surface, such as dry skin or other mammalian tissues, as a result of surface friction. In addition, many elastomeric surfaces display poor lubricity when contacting a damp surface as well. This is primarily due to a high coefficient of friction, or COF, of the elastomeric surface. Surfaces of elastomeric articles which exhibit a high coefficient of friction when sliding against another surface can be disadvantageous in uses where ease of donning and removal are beneficial to the use of the article. This property plays an important role in the use of medical gloves, such as examination and surgical gloves, where mechanical properties, tear resistance and tactile sensitivity during use are also beneficial features. Surgical gloves fabricated from natural rubber latex, for example, are difficult to don due to the high coefficient of friction between the glove material and the skin.

Various methods and techniques to improve the donning of gloves by reducing the coefficient of friction have been explored in the art. One such technique that has been employed is the use of talc or powders, such as calcium carbonate and starch, applied to the gloves during manufacture. Chemical methods have been explored as well to decrease the coefficient of friction of glove surface. One such method involves the halogenation of the surface of an elastomeric material to increase lubricity. However, halogenation techniques such as chlorination can adversely affect desirable mechanical properties of the material in articles such as gloves if the halogenation process is not well controlled.

A number of approaches to increase the lubricity of elastomeric articles (e.g., gloves) have been explored in the art, such as techniques using polymeric coatings, particulate micro-roughening of the surface, or combinations of both. Lubricant compositions containing silicone derivatives have been disclosed in U.S. Pat. No. 5,742,943 to Chen, which teaches flexible articles such as surgical gloves containing an elastomeric substrate layer having an elastomeric material which has been treated with a lubricant composition containing organo-modified silicone and amino-modified silicone compounds. U.S. Pat. No. 5,534,350 to Liou discloses a powder free glove containing an elastomeric layer with increased lubricity which has been treated with an aqueous dispersion of polyurethane together with a silicone emulsion. In medical applications, silicone has been widely used because of its lower surface energy, biocompatibility, e.g, high chemical and contamination resistance, and flexibility.

The use of polymeric surfaces embedded with microparticles to improve donning of gloves is known. See U.S. Pat. No. 5,792,531 to Littleton et al., for example. U.S. Pat. Nos. 5,405,666 and 5,395,666 to Brindle disclose an elastomeric glove with increased lubricity having a polymeric binding layer containing a surfactant and partially-protruding microparticles which produce a microroughening effect on the skin-contacting surface. U.S. Pat. Nos. 5,272,771 and 5,088,125 to Ansell et al. disclose an elastomeric glove with increased lubricity having a layer containing an ionic polyurethane in combination with particulate polyurethane, including acrylate or methacrylate co-polymers. U.S. Pat. No. 4,070,713 to Stockum discloses an elastomeric glove having a layer containing a binder and particulate microspheres. The binder can be composed of carboxylated styrene butadiene latex, and the particles can be composed of polyethylene, ethylenevinyl acetate co-polymers or epichlorohydrin cross-linked cornstarch.

There still exists the need for elastomeric articles such as medical gloves having improved donning properties while retaining the desirable mechanical and chemical properties associated with elastomeric articles. There is also a need in the medical community for powder-free medical gloves that avoid the disadvantages of conventional lubricity increasing techniques.

SUMMARY OF THE INVENTION

Applicants' invention is directed to an improved elastomeric article composed of a flexible, elastomeric material and a composite coating comprising a silicone-modified polymer in combination with silicone resin particles, and to a method of making such an article. It has been discovered by applicants that the chemical interaction between silicone-based polymers and silicone resin particles can be used to produce a coating which possesses a significantly reduced coefficient of friction, thereby improving the lubricity and donning properties of the article. The interaction between the siliconized polymer and particles enhance the binding of the particles and permit very thin coating layers to be applied to articles while still maintaining surface microroughness. Articles made according to the invention exhibit extended use without significant disassociation of the particles from the coating through wear. The invention is particularly useful as applied to elastomeric articles such as medical gloves (e.g., examination and surgical gloves) where donning or skin-contacting properties with respect to both dry and damp surfaces have historically been problematic.

In particular, the invention is directed to an elastomeric article having an elastomeric material and a coating layer adhered (e.g., bonded, fused, coupled) thereto and containing a composite comprising:

a) a silicone-modified polymer; and
b) silicone particles embedded and integrated throughout said polymer;
   wherein said coating layer is on a contacting surface of the article.

Elastomeric articles, such as surgical gloves, containing the coating layer and made according to the invention exhibit a topographically microroughened surface having a reduced coefficient of friction and improved lubricity and donning properties without the need for use of powders. The interaction between the components in the coating layer as well as the thickness of the coating layer and the ratio of polymer to particle collectively function to optimize the desirable properties of the article. Typically, the coating layer is applied to that surface of the article which will come into contact with skin when in use. In the case of a glove, the coating layer is on the interior surface of the glove when worn and absent from the exterior surface.

The elastomeric material used in the article can be composed of any natural or synthetic polymeric material which exhibits mechanical and chemical properties appropriate for the intended use of the article. In the case of surgical gloves, the elastomeric material must be flexible and tear-resistant with sufficient elongation and strength properties, and accommodate the tactile sensitivity requirements for gloves used in surgical procedures. Suitable elastomeric materials include, but are not limited to, those polymeric materials containing natural or synthetic rubber, polyurethane, conjugated diene homopolymers, conjugated diene co-polymers, conjugated diene and vinyl monomer copolymers, styrene block co-polymers (di-block and tri-block), and combinations thereof.

The coating layer adhered to the elastomeric material is a composite comprising a silicone-modified polymer in combination with silicone resin particles integrated and embedded therein. Any silicone-modified polymer which can adhere to the particular elastomeric material used and which can function to bind the silicone resin particles to a degree sufficient to inhibit detachment or delamination of the particles from the silicone-modified polymer, can be used. Silicone-modified polymers which can be used include those polymeric structures which can have silicone groups covalently attached to the chemical structures. Suitable silicone-modified polymers include, but are not limited to, silicone-modified polyurethanes, acrylics, vinyl, alkyl, esters, EPDM and nitriles. Preferred silicone-modified polymers are silicone-modified polyurethanes.

Homogenous or, alternatively, heterogenous mixtures of different silicone-modified polymers can be used in accordance with the invention provided they can interact with the silicone groups of the particles. Furthermore, polymers not modified with silicone groups can be present in the coating layer as well provided they do not interfere with the functionality of the silicone-modified polymers for purposes of the invention.

In general, the silicone resin particles used in accordance with the invention are those physically adapted for incorporation or integration into polymers and chemically compatible with the particular polymer used. Chemically, the silicone particles used must contain a degree of exposed silicone functional groups on the surface sufficient to chemically interact with the silicone groups bonded to the silicone-modified polymer(s) used in the composition.

The invention also includes a method of making an elastomeric article containing an elastomeric material and coating layer comprising the composite according to the invention. The method of making an elastomeric article comprises the steps of:

a) forming a first layer of elastomeric material;
b) adhering a second, friction-reducing coating layer to said first layer, said coating layer being formed from a dispersion comprising a silicone-modified polymer in combination with silicone particles integrated therein.

In a further embodiment, the coated article is subjected to a chlorination process to produce a powder-free article.

Accordingly, the silicone-modified polymer and silicone resin particle composite can be applied to elastomeric materials to decrease the coefficient of friction between the interior surface of the article and the skin of the wearer, for example. Articles such as gloves can be made by using conventional techniques in the art, which generally involve the use of a mold and the steps of dipping and curing to form layers on the mold which are subsequently removed intact.

In general, a method of making a glove according to Applicants' invention involves the initial steps of forming a coagulant layer and elastomeric material layer onto a mold, leaching, and subsequently dipping the glove into an aqueous dispersion and curing the glove to produce a friction-reducing coating layer on the first material. Accordingly, the dispersion contains the ingredients which produce the coating layer according to the invention, i.e., the silicone-modified polymer and silicone resin particles, as well as additional ingredients well-known in the art which can be used in the dispersion which include surfactants, lubricants, releasing agents, defoamers, curing agents, pigments, plasticizers, antioxidants, and the like. After curing, the gloves are stripped from the mold, wherein the glove is inverted so as to position the coating layer on the interior surface and the uncoated elastomeric material on the exterior surface. The glove can be further subjected to a chlorination process to produce a powder-free glove.

The invention also includes an aqueous dispersion for coating elastomeric materials to increase lubricity comprising a silicone-modified polymer and silicone particles integrated therein.

Articles made according to applicants' invention contain a contacting (e.g., skin-contacting) layer in which the silicone groups on both the silicone-modified polymer and silicone resin particles interact in a coating layer to reduce the coefficient of friction between the treated surface and the skin. Furthermore, the chemical affinity between the particles and the modified polymer enhances the binding of the particles to the coating layer and thereby reduces detachment, disassociation or delamination of the particles from the skin-contacting surface. Accordingly, one of the advantages associated with applicants' invention is the reduced coefficient of friction and increased lubricity afforded to elastomeric articles without the use of powders. When the invention is applied to surgical gloves, for example, the gloves exhibit ease of donning while at the same time retaining the other functional features important during their use, such as strength, flexibility, and tactile sensitivity.

Another advantage of the invention is that the chemical affinity between the silicone functional groups on both the polymer and particulate components of the coating layer permits the application of a thinner coating layer while still preserving the adhesion between the particles and the layer.

Yet another advantage of the invention is that the properties of reduced coefficient of friction and increased lubricity of the coated article (e.g., glove) are substantially maintained throughout the halogenation or chlorination treatment process of the article.

DETAILED DESCRIPTION OF THE INVENTION

Figure 1:
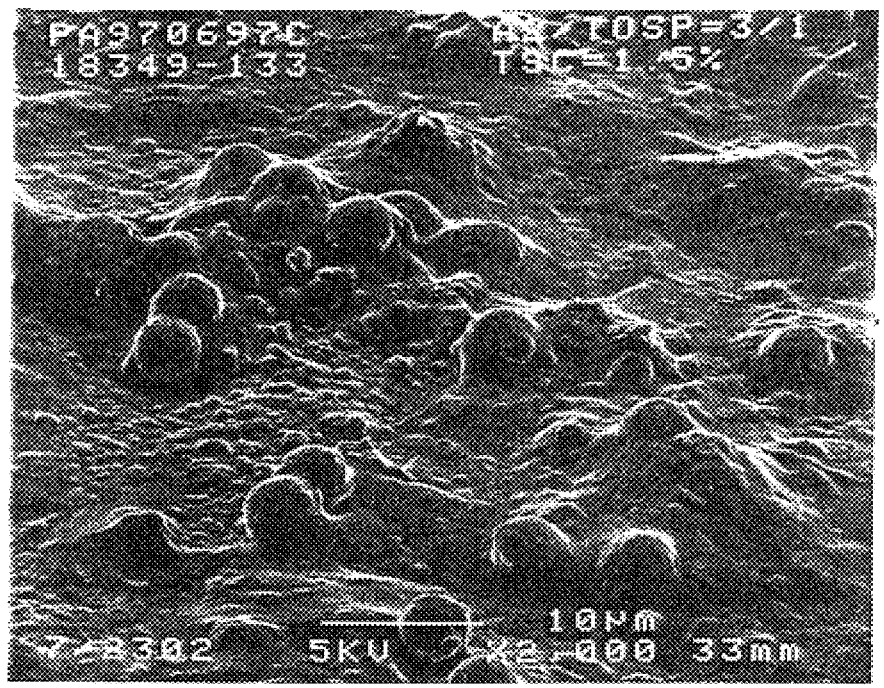
FIGS. 1 and 2 are SEM photographs of the surface of elastomeric article samples prepared according to the invention.

As used herein, the terms "elastomer" and "elastomeric" when used in conjunction with reference to articles or materials is meant to refer to a polymer which exhibits characteristics of rubber, e.g., the capability of the article or material to flex and return to the original configuration. The term "skin" by itself is meant to include human or other mammalian skin or tissues. The term "contacting" when used to describe a surface refers to portion of an article, interior or exterior, which benefits from the increased lubricity as a result of the surface being treated according to applicant's invention. The term "modified" when used in reference to polymers or polyurethanes refers to chemical modification or derivatives of the structure. When used in reference to "silicone-modified," the term refers to compounds wherein silicone groups have been incorporated into their chemical structure. The term "alkyl" refers to a group or linkage involving saturated hydrocarbons, such as a methyl group. The term "powder-free" when used herein to describe an elastomeric article or glove is meant to indicate the absence of powders applied to the surface which can be accomplished in accordance with the manufacturing process, e.g., inclusion of a chlorination step using a powderless coagulant.

Applicants' invention can be applied to any elastomeric article where donning or skin-contacting properties with respect to both dry and damp surfaces would benefit from an improvement thereupon or where obtaining such properties has historically been problematic. For purposes of illustration, the applicant's invention will be described in the context of medical gloves.

Applicants' invention includes an elastomeric article composed of an elastomeric material and a coating layer adhered (bonded, fused, coupled) thereto and containing a composite comprising:
 a) a silicone-modified polymer; and
 b) silicone resin particles embedded and integrated throughout said polymer;
  wherein said coating layer is on the contacting (e.g., skin-contacting) surface of the article.

Elastomeric materials suitable for use in the article can be composed of any natural or synthetic polymeric material which exhibits mechanical and chemical properties appropriate for the intended use of the article. In the case of surgical gloves, the elastomeric material must be flexible, tear-resistant, possess sufficient elongation modulus, and strength properties, and accommodate the tactile sensitivity requirements for gloves used in surgical procedures. Suitable elastomeric materials include, but are not limited to, those polymeric materials containing natural or synthetic rubber, polyurethane, conjugated diene homopolymers, conjugated diene co-polymers, conjugated diene and vinyl monomer copolymers, and combinations thereof.

Suitable conjugated dienes can include those containing heteroatoms such as halogenated conjugated dienes. Preferred conjugated dienes include butadiene (1,3-butadiene), isoprene (2-methyl-1,3-butadiene), 2,3-dimethyl-1,3-butadiene, 1,3-pentadiene (piperylene), 1,3-hexadiene, chloroprene (e.g., neoprene), and the like. Preferred vinyl monomers include alkenyl arenes, such as styrene (e.g., o-methylstyrene, p-methylstyrene, p-tert-butylstyrene, 1,3-dimethylstyrene, alpha-methylstyrene, and other ring-alkylated styrenes); alkylenes (e.g., ethylene, propylene, butylenes); and acrylonitrile.

Copolymers can be random, tapered or block copolymers. Preferred rubbers can be natural or synthetic, including polyurethane, neoprene (homopolymer if conjugated diene chloroprene), nitrile rubber (copolymer of conjugated diene butadiene and vinyl monomer acrylonitrile), block copolymers of styrene and butadiene, block copolymers can include styrene-ethylene-butylene-styrene (S-EB-S) and styrene-isoprene (SIS) block copolymers.

The coating layer adhered to the elastomeric material contains a composite comprising a silicone-modified polymer in combination with silicone resin particles integrated and embedded therein. Any silicone-modified polymer which can be adhered to the particular elastomeric material used as described and which can function to bind the silicone resin particles to a degree sufficient to inhibit detachment, disassociation or delamination of the particles from the silicone-modified polymer can be used. Silicone-modified polymers which can be used include those polymeric structures which contain a silicone group covalently bonded or attached to the polymeric compound structure. Silicone-functionalized polymers can be prepared by covalent attachment of silicone moieties to the polymeric structure through a number of covalent linkages, including but not limited to siloxy groups, for example. Other linking groups can be used as well, such as those disclosed by U.S. Pat. No. 5,589,563 to Ward et al., the entire text of which is incorporated herein by reference.

Suitable silicone-modified polymers include, but are not limited to, those selected from the group consisting essentially of silicone-modified polyurethanes (such as those which can be prepared according to Ward et al., U.S. Pat. No. 5,589,563 and available from Polymer Technology Group, Emeryville, Calif., and NeoRez XR9649 available from Zeneca Resins, Wilmington, Mass.), silicone-modified nitrites, silicone-modified acrylics (such as silicone/acrylate polymers (APR) poly(dimethylsiloxane)-g-polyacrylates available from Minnesota Manufacturing and Mining Co., St. Paul, MN; and copolymers of monomers and alkyl acrylates as found in U.S. Pat. 5,700,585 to Lee and available from Avery Dennison Corporation, Pasadena, Calif.), silicone-modified vinyls (such as those disclosed in U.S. Pat. No. 5,777,052 to Kobayashi et al. and available from Dow Corning Toray Silicone., Ltd., Tokyo, Japan); silicone-modified alkyls (such as those disclosed in U.S. Pat. No. 4,535,126 to Lida and available from Kansai Paint Co., Ltd., Hyogo, Japan), silicone-modified esters (such as silicone-modified polyesters disclosed in U.S. Pat. No. 4,199,648 to Curry et al. and available from General Electric Co., Pittsfield, Mass.; and disclosed in U.S. Pat. 4,035,332 to Gomyo et al. and available from Shin-Etsu Chemical Co., Tokyo, Japan), and silicone-modified EPDM (such as those disclosed in U.S. Pat. No. 5,969,022 to Bova et al. and available from Uniroyal Chemical Company, Inc., Middlebury, Conn.).

Preferred silicone-modified polymers are silicone-modified polyurethanes. Silicone groups can be attached to polyurethanes according to the method described in U.S. Pat. No. 5,589,563 to Ward et al., for example, the entire text of which is incorporated herein by reference.

Homogenous or, alternatively, heterogenous mixtures of different silicone-modified polymers can be used in accordance with the invention provided they can interact with the silicone groups of the particles. In yet another embodiment, polymers not modified with silicone groups can be present in the coating layer composition as well, provided no phase separation occurs in their use during the coating process and they do not interfere with the functionality of the silicone-modified polymers for purposes of the invention.

The silicone resin particles used in accordance with the invention are those physically adapted for incorporation or integration into polymers and chemically compatible with the particular polymer used. Chemically, the silicon particles used must contain a degree of exposed silicone functional groups on the surface sufficient to chemically interact with the silicone groups bonded to the silicone-modified polymer (s) used in the composition. Examples of suitable silicone particles which can be used in the invention include, but are not limited to, those available from GE Silicones, Waterford, N.Y., Dow Corning 22 and 23 Additives cured silicone elastomeric powders, Dow Coming Corporation, Midland, Mich., U.S. Pat. No. 5,188,899 to Matsumoto et al. and European Pat. EP 822,232 (Toshiba Silicone Co., Ltd., Tokyo, Japan), U.S. Pat. No. 4,742,142 to Shimizu et al. (Toray Silicone Co., Ltd., Tokyo, Japan), and U.S. Pat. No. 4,962,165 to Bortnick et al. (Rohm and Haas Co., Philadelphia, Pa.).

Silicone resin particles which can be used include those containing molecular network structures of siloxane groups, such as siloxane-bonded alkyl groups, for example. One particular type of silicone resin particle which contains siloxane bonds and silicone groups bonded to methyl groups is those of the TOSPEARL™ series silicone particles (available from Toshiba Silicone Co., Ltd.), more specifically TOSPEARL 145.

Silicone particle size will vary according to the desired micro-roughening effect as it is affected by the by the thickness of the coating layer and silicone-modified polymer formulation used. Particle size can be generally described as fine particle size and can include particles having a diameter ranging from about 0.1 microns to about 15.0 microns, and typically from about 0.1 microns to about 12.0 microns. In the case of certain TOSPEARL particles such as TOSPEARL 145, for example, particle diameter range can vary from about 0.2 microns to about 0.8 microns.

Silicone particle shape is generally spheroid or ovoid, although variations in both size and shape will likely be present. For example, the silicone particles can be in the configuration of elongate fibers. Mixtures of varying geometrical particle configurations can be used as well. Particle surface morphology is generally smooth, although variations in surface morphology and structure are also possible. For example, roughened or porous particle structures and mixtures thereof can be used.

Silicone resin particles are present in the coating layer in an amount sufficient to produce the desired micro-roughness surface texture in view of the silicone-modified polymer and coating thickness to be applied. Generally, the silicone particles will be present in a ratio of polymer to particle ranging from about 10 to 1 (10/1) to about 1 to 1 (1/1), preferably in a ratio of about 3 to 1 (3/1).

Mixtures of two or more different silicone particles can be used for the silicone particles component of the coating layer, as well as mixtures of particles having varying sizes and shapes.

Generally, the thickness of the coating layer applied to the skin-contacting surface of the article varies according to the particular silicone-modified polymer, silicone particles, and particle size and amount. As a result of the invention, very thin coating layers can be applied as a result of the chemical affinity between the siliconized polymer and particles while maintaining the desired microroughness and donning properties. Percent total solid content (% TSC) of the dispersion, as it relates to coating viscosity and thickness and particle size, can therefore range from about 1.0% to about 5.0%, and even range between from about 1.0% to about 3.0% without significant departure from the desired microroughness topography afforded by the adhered particles.

Coating layer thickness and composite formulation can be selected so as to optimize the micro-roughening effect desired for the particular article to be treated.

The invention also includes a method of making an elastomeric article containing an elastomeric material and coating layer comprising the composite according to the invention. In general, the method of making a glove according to applicants' invention involves the steps of forming a first layer of the elastomeric material onto a mold and subsequently dipping into a dispersion to adhere a second, friction-reducing coating layer to the first material. The glove is then heated/cured and stripped from the mold, whereby the glove is inverted so as to position the coating layer on the interior surface and the untreated elastomer material on the exterior surface. The glove can then further undergo the chlorination process to produce a powder-free glove.

A typical procedure for making gloves is as follows. The initial step of forming a glove involves pre-heating a glove former (i.e., mold) to a temperature of from about 40° C. to about 60° C. in an oven and dipping the former into a stirred, alcohol-based coagulant dispersion maintained at a temperature less than about 55° C. The coagulant-dipped layer is then air dried. The coagulant-coated former is dipped into a compounded neoprene copolymer latex maintained at a temperature of from about 20° C. to about 28° C. for a time period sufficient to produce the desired glove thickness. The neoprene copolymer latex can be compounded with stabilizers, crosslinking agents, vulcanization activators and accelerators, antioxidants, antiozonants, and pigments. The coagulated latex-coated former is then removed and leached in water at a temperature of about 60° C. The former is then dipped into a dispersion to form a coating layer on the neoprene rubber layer. The cuff of the coated gloves can then be beaded and the former placed in an oven at a temperature of from about 120° to about 150° C. for a period of about 20 minutes in order to cure the glove. The former with the glove are then removed and cooled.

Gloves prepared in accordance with the invention can be powder-free gloves. To produce a powder-free surgical glove, a post-process chlorination step is performed. Accordingly, the coated glove is inverted and loaded into the chlorinator. The glove is pre-rinsed and chlorinated while being tumbled for about 4 minutes. The glove is neutralized using, for example, ammonium hydroxide and sodium thiosulfate, for a period of about 2 minutes. Afterwards, the glove is rinsed and tumbled with water, and then loaded into the washer/extractor, which washes the glove and extracts twice. The glove is then loaded into a dryer/lubricator and dried at a temperature of from about 95° to about 115° F. for several minutes. During heating, the gloves can be sprayed with a lubricant solution. The gloves are cooled for about 10 minutes, inverted, and loaded into a dryer and dried at a temperature of from about 95° F. to about 115° F. for a period of from about 25 to about 45 minutes until the gloves are completely dried. The gloves are then cooled and ready for packaging.

The dispersion used to prepare the coating layer in accordance with the invention is an aqueous dispersion which contains a composition comprising a silicone-modified polymer and silicone particles as described herein, as well as additional ingredients well-known in the art such as surfactants, lubricants, defoamers and curing agents, and the like.

Surfactants which can be used in the coating layer include any surfactant which is suitable for use on skin and other tissue and does not cause allergic or otherwise undesirable reactions to the user. Amphoteric, anionic, cationic and nonionic surfactants, and long-chain fatty amines can be used. Cationic surfactants which can be used include cationic surfactants containing at least one lipophilic moiety (such as alkyl, aralkyl, aryl, or cycloalkyl group) and a hydrophilic moiety (such as an ammonium group). One example of a cationic surfactant is 1-hexadecylpyridinium chloride monohydrate. Other surfactants which can be used include polyalkylene oxide-modified polydimethylsiloxanes, such as SILWET™ surfactants (available from Witco), BYK™-348 available from BYK Chemie, branched ethoxylated nonylphenols such as Igepal CO-730 (available from Rhone-Poulenc, N.J.).

Stabilizers can be used in conjunction with both the silicone-modified polymer and silicone particle components of the dispersion and selected to optimize the uniform distribution of particles over the surface of the material treated based upon the particular modified polymer or polymers and particle type to be used. Preferred are electrostatic stabilizers, such as anionic stabilizers.

Defoamers, curing agents, lubricants and releasing agents, as well as other conventional dispersion additives, are available and well-known to those in the art. Pigments, plasticizers, antioxidants and the like can also be used.

Both the thickness of the elastomeric material and coating layer used in the article can vary according to the desired properties or requirements of the article, as well as the preferences of the manufacturer.

In a further embodiment, the base material of the elastomeric articles according to the invention can include other layers or materials in addition to those specifically mentioned above. For example, the article or glove can include more than one layer of base elastomer material, one of which contacts the coating layer containing the composite according to the invention. Furthermore, the elastomeric materials used in the article can further include embedded structural support materials, such as metallic or polymeric meshing or lattice structures, to enhance mechanical strength of the article.

In an alternative embodiment, the coating layer of the invention can be applied to only a portion of a glove or other article, as opposed to an entire surface.

Articles such as gloves which have been prepared according to the method of the invention contain a microroughened skin-contacting surface wherein the silicone resin particles are embedded and partially exposed topographically on the surface of the article. The chemical interaction between the silicone functional groups on both the modified polymer and the surface of the particle forms an integration between the structures thereby producing an affinity between the components which functions to bind the particles securely onto the coating layer and prevent detachment or delamination of the particles. The microroughening, or topography, of the particles provide a surface texture which significantly reduces the coefficient of friction and therefore increases the lubricity of the article. Coefficients of friction of less than about 0.6 as measured by ASTM D 1894-95 can be obtained on elastomeric articles prepared according to the invention. Coefficients of friction of even less than about 0.5 can be obtained.

Another feature of the invention is that the properties of reduced coefficient of friction and increased lubricity of the coated article (e.g., glove) are substantially maintained throughout the halogenation or chlorination treatment process of the article and the donning properties of the article retained, despite the potentially adverse effects that the chlorination process can have on the physical and chemical properties of such materials as a result of such treatment.

Objects and advantages of this invention will now be illustrated by the following examples, but the particular materials and amounts thereof recited in these examples as well as other conditions and details, should not be construed to unduly limit this invention.

EXAMPLE 1

Preparation of Latex Glove With a Silicone-Modified Polyurethane/ Silicone Resin Particle Coating In general, the process of making a glove according to the invention is as follows:

A clean hand-shaped mold having an exterior surface is initially coated with a coagulant layer and then dipped into a first bath containing elastomeric latex, preferably a natural rubber latex. A film is formed over the mold surface and the mold is subsequently removed from the first bath. The mold covered with the film is then heated to gel and fuse the latex. Subsequently, the mold and latex film is then cooled, leached, and dipped into a second bath, which contains an aqueous suspension of the silicone-modified polyurethane and silicone particles, as well as the other ingredients used for the second, friction-reducing coating layer. A second film is then formed over the mold and latex layer. This coating contains the silicone-modified polyurethane having the silicone particles mixed therein. Then, the mold, first and second layers are removed from the second bath and cured and dried, thereby adhering the first layer (latex) and the friction-reducing coating layer.

Accordingly, a two-layered, unitary article in the form of a glove is produced over the surface of the mold. The glove is then stripped (i.e., peeled or separated) from the mold surface such that the exterior surface of the mold-bound glove becomes inverted and becomes the interior surface of the glove.

The gloves can be subjected to further processes or treatments in the art, such as chlorination.

EXAMPLE 2

Dispersion Formulation (2% total solid content) for Coating Layer

Natural rubber latex was applied to a glove-shaped mold according to the general steps described above. In this example, a glove former (i.e., mold) was dipped into a water based or alcohol based coagulant dispersion, the formulation of which is well-known to those skilled in the art. The deposited coagulant layer was then dried on the mold. The mold was then dipped into compounded Neoprene™ rubber latex and allowed to dwell for a few seconds to coagulate the rubber latex. The coagulated latex was then leached in a water leaching tank.

The latex-covered mold was then dipped into a bath of an aqueous dispersion having a total solid content (TSC) of 2% and the following formula:

| Ingredient: | Compound: | Amount: | Available from: |
|---|---|---|---|
| Si-modified polymer | Si-polyurethane | 100 parts | PTG, CA |
| Si resin particle | Tospearl 145 | 33.1 parts | GE Silicones, N.Y. |
| Surfactant | Igepal CO-730 | 1.9 parts | Rhone-Poulenc, N.J. |
| Surfactant | BYK-348 | 5.6 parts | BYK Chemie |
| Lubricating agent | GE SM2140 | 46.9 parts | GE Silicones, N.Y. |

The latex and coating layer were cured in an oven and the glove was finally stripped from the mold. The gloves were post-treated by turning over, chlorination, neutrilization, rinsing, lubrication and drying.

EXAMPLE 3

Dispersion Formulation (3% total solid content) for Coating Layer

The above process was performed in a similar manner, except the coating layer dispersion employed in the process had the following composition:

| Ingredient: | Compound: | Amount: | Available from: |
|---|---|---|---|
| Si-modified polymer | NeoRez XR9649 | 100 parts | Zeneca, CA |
| Si resin particle | Tospearl 145 | 33.1 parts | GE Silicones, N.Y. |
| Surfactant | Igepal CO-730 | 1.9 parts | Rhone-Poulenc, N.J. |

-continued

| Ingredient: | Compound: | Amount: | Available from: |
|---|---|---|---|
| Surfactant | BYK-348 | 5.6 parts | BYK Chemie |
| Lubricating Agent | GE SM2140 | 46.9 parts | GE Silicones, N.Y. |

EXAMPLE 4

Comparative Data of Particle Composition on Coefficient of Friction

Neoprene gloves containing four coating dispersions were prepared, each dispersion having different particle compositions in order to compare the coefficient of friction of the glove sample resulting from the respective particles.

The dispersion formulations were prepared having the following formulations summarized in Table 1.

TABLE 1

Formulations Having Different Particle Types

| Particle: | Ingredients: | Amount (parts): |
|---|---|---|
| Silicone | Si-modified polyurethane | 1.07 parts |
|  | Tospearl 145 | 0.36 |
|  | Igepal CO-730 | 0.02 |
|  | BYK-348 | 0.04 |
|  | GE SM 2140 | 0.50 |
|  | DDI (deionized water) | 98.00 |
| PE | Si-modified polyurethane | 0.85 parts |
|  | ACX 1221 (PE) | 0.28 |
|  | Igepal CO-730 | 0.03 |
|  | BYK-348 | 0.09 |
|  | GE SM 2140 | 0.75 |
|  | DDI | 98.0 |
| PTFE | Si-modified polyurethane | 0.85 parts |
|  | HC 9174 (PTFE) | 0.28 |
|  | Igepal CO-730 | 0.03 |
|  | BYK-348 | 0.09 |
|  | GE SM 2140 | 0.75 |
|  | DDI | 98.0 |
| Silica | Si-modified polyurethane | 1.07 parts |
|  | W-500 (Silica) | 0.36 |
|  | Igepal CO-730 | 0.02 |
|  | BYK-348 | 0.06 |
|  | GE SM 2140 | 0.50 |
|  | DDI | 98.0 |

Each dispersion contained 2% Total Solid Content (TSC) and a ratio of 3/1 silicone-modified polymer to silicone particle. The silicone-modified polymer used in each formulation was a silicone-modified polyurethane from Polymer Technology Group, CA. The particle compositions compared were TOSPEARL 145 (available from GE Silicones, NY), PE (polyethylene) (Ethylene-Propylene-Maleic Anhydride Copolymer A-C-X 1221 available from Honeywell International, Morristown, N.J.), PTFE (Hydrocerf 9174 available from Shamrock Technologies, Inc., Newark, N.J.), and Silica (Syloid W 500 available from Grace Davison, W. R. Grace & Co., Baltimore, Md.)

The coefficient of friction was determined using ASTM (Standard Test Method) for Static and Kinetic Coefficients of Friction of Plastic Film and Sheeting) identified as Designation: D 1894-95 (1995), which measures starting and sliding friction of plastic film and sheeting when sliding over itself or other substances at specified test conditions in terms of the ratio of frictional force to the force acting perpendicular to the two contacting surfaces. The COF was measured for all four samples, each under both dry and wet surface-contacting conditions.

Wet COF was determined based on ASTM D 1894-95 with modified test procedures. Accordingly, a glove sample with an area of about 2.5 inches by 2.5 inches is attached to a sled whereby the tape does not come into contact with the metal planar surface along which the sled will be pulled. About 10 to 20 ml. of water is poured onto the metal plane and the Instron calibrated to zero pounds of force. The sled containing the sample is attached to a metal cable and placed atop the water. The instrument is activated and the sled is pulled a distance of 7 inches with a cross-head speed of 20 inches per minute. The device charts a graph of pounds of load force between 0 to 7 inches with a mass of 200 grams, and the wet kinetic COF is calculated therefrom.

The results are summarized in Table 2 below.

TABLE 2

Effect of particle Composition on Kinetic Coefficient of Friction (COF)

| Particle: | Wet COF: | Dry COF: |
|---|---|---|
| TOSPEARL 145 | 0.363 | 0.282 |
|  | 0.402 | 0.413 |
|  | 0.365 | 0.401 |
| PE | 0.501 | 0.421 |
|  | 0.567 | 0.580 |
|  | 0.487 | 0.479 |
| PTFE | 0.449 | 0.387 |
|  | 0.453 | 0.428 |
| Silica | 0.550 | 0.557 |
|  | 0.652 | 0.640 |
|  | 0.514 | 1.049 |

As can be seen from the resulting data, when compared to gloves with coating layers using particles composed of polyethylene (PE), tetrafluoroethylene (PTFE), and silica, the glove samples containing the coating layer with the silicone particles TOSPEARL 145 exhibit the lowest coefficient of friction (COF).

EXAMPLE 5

Comparison Between Interaction of Different Polymers with Silicone Resin

The interactions between coatings containing silicone-modified polyurethanes and silicone resin particles were compared to coatings containing non-silicone modified polymers and silicone resin particles was examined and compared using natural rubber gloves treated with different coating formulations.

The silicone-modified polyurethanes used are available from Polymer Technology Group, Inc., Emeryville, Calif. and the silicone-modified polyurethane NeoRez 9649 is available from Zeneca Resins, Wilmington, Mass. TYLAC 68077 and 68074 (available from Reichhold Chemicals, Inc., Research Triangle Park, NC) are synthetic nitrile latex (i.e., carboxylated butadiene-acrylonitrile copolymers) and are absent attached silicone groups.

Samples were prepared in accordance with the conventional dipping and coating procedures and were coated using dispersions having the following formulations:

TABLE 3

Dispersion Formulations Using Various Polymers

| Sample: | Ingredients: | % (Percent) | Parts per 100 latex |
|---|---|---|---|
| 1 | Si-modified polyurethane | 2.0% | 100 parts |
|   | Tospearl 145 | 1.0 | 50 |
|   | DDI (deionized water) | 97.0 | — |
| 2 | Si-modified polyurethane | 2.0% | 100 parts |
|   | Tospearl 145 | 1.0 | 50 |
|   | Igepal CO-730 | 0.03 | 1.5 |
|   | BYK 348 | 0.09 | 4.5 |
|   | GE SM 2140 | 0.75 | 37.5 |
|   | DDI | 96.13 | — |
| 3 | NeoRez XR9649 | 1.5% | 100 parts |
|   | Tospearl 145 | 0.5 | 33.1 |
|   | Igepal CO-730 | 0.03 | 2.0 |
|   | BYK 348 | 0.09 | 6.0 |
|   | GE SM 2140 | 0.75 | 50.0 |
|   | DDI | 96.63 | — |
| 4 | Tylac 68074 | 4.04% | 100 parts |
|   | Tospearl 145 | 1.35 | 33.1 |
|   | SMO | 0.02 | 0.5 |
|   | BYK-348 | 0.02 | 0.5 |
|   | Sulfur | 0.05 | 1.0 |
|   | ZDBC | 0.05 | 1.0 |
|   | ZnO | 0.14 | 3.0 |
|   | DDI | 94.5 | — |
| 5 | Tylac 68077 | 4.0% | 100 parts |
|   | Tospearl 145 | 1.35 | 33.1 |
|   | SMO | 0.02 | 0.5 |
|   | BYK-348 | 0.02 | 0.5 |
|   | Sulfur | 0.05 | 1.0 |
|   | ZDBC | 0.05 | 1.0 |
|   | ZnO | 0.14 | 3.0 |
|   | DDI | 94.5 | — |
| 6 | Tylac 68074 | 4.04% | 100 parts |
|   | SMO | 0.02 | 0.5 |
|   | BYK-348 | 0.02 | 0.5 |
|   | Sulfur | 0.05 | 1.0 |
|   | ZDBC | 0.05 | 1.0 |
|   | ZnO | 0.14 | 3.0 |
|   | DDI | 95.8 | — |
| 7 | Tylac 68077 | 4.04% | 100 parts |
|   | SMO | 0.02 | 0.5 |
|   | BYK-348 | 0.02 | 0.5 |
|   | Sulfur | 0.05 | 1.0 |
|   | ZDBC | 0.05 | 1.0 |
|   | ZnO | 0.14 | 3.0 |
|   | DDI | 95.8 | — |

The first five samples were prepared using coating formulations with TOSPEARL 145 as the silicone resin particle. The sixth and seventh samples were prepared without TOSPEARL.

The coefficient of friction for each sample was tested under both dry and wet conditions as measured according to ASTM D 1894-95 as previously described.

The results are summarized in Table 4 below.

TABLE 4

Comparative Friction Data Between Polymer Formulations and TOSPEARL 145

| Sample # | Polymer: | TSC %: | Ratio: | Dry COF | Wet COF |
|---|---|---|---|---|---|
| 1 | Si-modified polyurethane | 3% | 3/1 | 0.448 | 0.448 |
|   |   |   |   | 0.480 | 0.499 |
| 2 | Si-modified polyurethane | 4% | 3/1 | 0.294 | 0.386 |
|   |   |   |   | 0.318 | 0.392 |
| 3 | NeoRez XR9649 | 2% | 3/1 | 0.429 | 0.457 |
|   |   |   |   | 0.521 | 0.483 |
| 4 | Tylac 68074 | 5% | 3/1 | 0.558 | 0.592 |
|   |   |   |   | 0.575 | 0.597 |
| 5 | Tylac 68077 | 5% | 3/1 | 0.737 | 0.656 |
|   |   |   |   | 0.637 | 0.584 |
| 6 | Tylac 68074 | 5% | N/A | 0.829 | 0.683 |
|   |   |   |   | 0.923 | 0.664 |
| 7 | Tylac 68077 | 5% | N/A | 0.966 | 0.697 |
|   |   |   |   | 1.117 | 0.667 |

As can be seen from the results, the samples containing coating layers with both silicone-modified polymers and silicone resin particles exhibited a lower coefficient of friction when compared to the coatings containing non-silicone modified polymers and silicone resin particles. The coatings of samples 6 and 7 containing non-silicone-modified polymers without silicone particles exhibited significantly higher coefficients of friction than the remaining samples.

In conclusion, the samples containing silicone-functionalized groups on both the polymer and the resin particles had noticeably lower coefficients of friction than the other samples. Therefore, articles treated according to the invention have increased lubricity.

EXAMPLE 6

Particle Binding Effectiveness (SEM) Data

Representative photomicrographs of samples of the skin-contacting (interior) surface of gloves treated with the coating layer according to the invention were obtained. The photographs were taken using Low Voltage Scanning Electron Microscopy (LVSEM) with a JEOL JSM-6300F Field Emission Scanning Electron Microscope. SEM data illustrating the binding effectiveness of the coating layer with regard to the silicone particles is shown in FIGS. 1 through 4.

Figure 2:
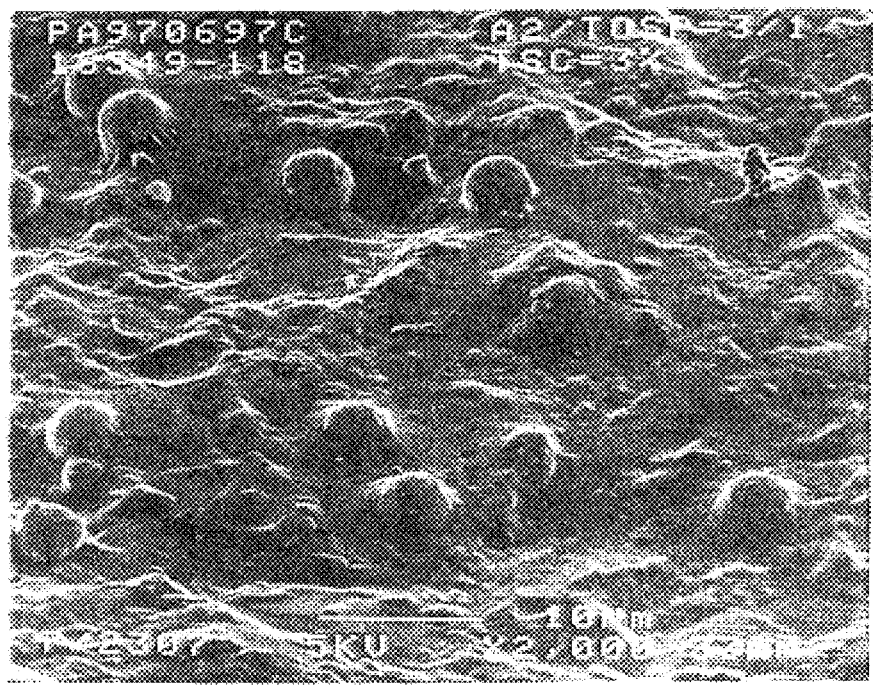

FIGS. 1 and 2 are SEM photographs of Neoprene™ glove sample having a coating layer formed using a dispersion with a 3 to 1 ratio of a silicone-modified polyurethane (from Polymer Technology Group) and TOSPEARL 145 as the silicone resin particle. The sample in FIG. 1 was formed from a dispersion having a TSC of 1.5% and FIG. 2 formed from a dispersion having TSC of 3%.

As can be seen from the photographs in FIGS. 1 and 2, the particles on the coating layer appear to be sufficiently embedded in the coating layer with the application of dispersions having a TSC as low as 1.5% while still accomplishing microroughness of the skin-contacting surface.

Figure 3:
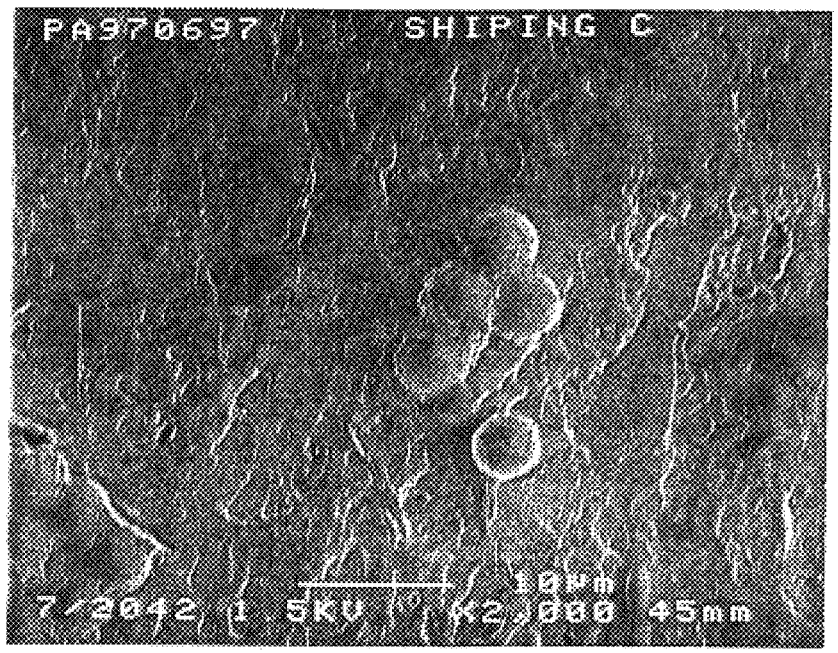
FIGS. 3 and 4 are SEM photographs of the surface of an identical elastomeric article sample prepared according to the invention in both the relaxed and stretched condition, respectively.
Figure 4:
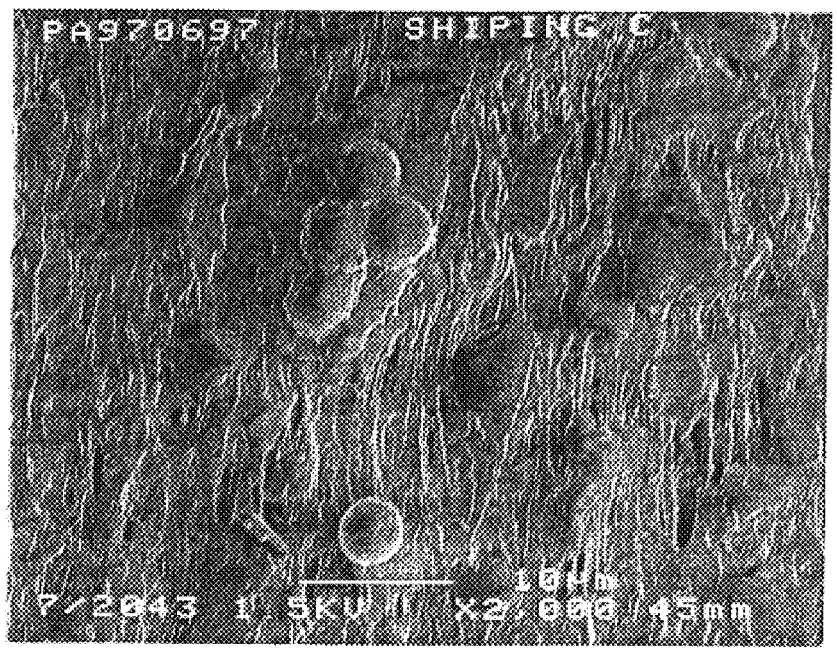

FIGS. 3 and 4 are photographs of samples prepared with a coating layer dispersion having the silicone-modified polyurethane (from Polymer Technology Group) and TOSPEARL 145 as the silicone particle in a 3 to 1 ratio and TSC of 2%. The samples were then photographed in both relaxed, non-stretched and stretched condition and then compared. The sample seen in FIG. 3 is in the relaxed condition, whereas the same sample is shown in 500% stretched condition in FIG. 4.

As can be seen from the photographs, the glove samples treated with a coating layer according to the invention demonstrate that the silicone particles remain adhered to the coating layer when stretched without a significant degree of detachment.

EXAMPLE 7

Effect of Chlorination on Coefficient of Friction (COF)

Neoprene glove samples were coated according to the invention and examined before and after being subjected to chlorination process to evaluate the effect of chlorination on the coefficient of friction values.

Each of the gloves (Gloves 1 and 2) was coated with one of the two dispersions prepared in accordance with the invention as described herein. One dispersion containing silicone-modified polyurethane (from Polymer Technology Group) and TOSPEARL 145 and the other containing the silicone-modified polyurethane NeoRez XR9649 (from Zeneca Resins) and TOSPEARL 145 were used to coat the samples.

The gloves were subjected to the chlorination process. The chlorination process used involved the general steps of chlorination (accompanied by chlorine concentration preparation and testing), rinsing and extraction, a first drying application, inversion of the wet gloves, and a final drying. In the first step, a chlorine and water solution were titrated to calculate parts per million chlorine. The chlorination value ($Cl_2$ analysis) used was 665 ppm and the gloves subjected to chlorination for a period of 30 minutes. The gloves were then loaded into the washer/extractor and subjected to repeated filling and spraying, draining and extracting steps for a total of about 25 minutes. The gloves were then transferred to the dryers for the first dry application, wherein the gloves were dried in four repeated heated tumbles at a temperature setting of about 105° F.±5° F. and a final cool down cycle for a total of 48 minutes. The gloves were then inverted using a vacuum invertor and removed. The gloves were finally dried in two cycles of heat drying and cooling, the heat drying steps performed at a temperature of about 105° F.±5° F. for a period of 41 minutes. Samples of each glove were then taken and the dry and wet coefficient values (COF) were obtained in accordance with ASTM D 1894-95 as described above. The results are found in Table 5 below:

TABLE 5

Pre- and Post-Chlorination COF Data

| Formulation (3/1 ratio, TSC 3%) | Chlorination | Glove 1 (dry COF) | Glove 1 (wet COF) | Glove 2 (dry COF) | Glove 2 (wet COF) |
| --- | --- | --- | --- | --- | --- |
| Silicone-modified polyurethane and Tospearl | Before | 0.348 | 0.356 | 0.337 | 0.368 |
| Silicone-modified polyurethane and Tospearl | After | 0.306 | 0.307 | 0.314 | 0.341 |
| NeoRez and Tospearl | Before | 0.414 | 0.405 | 0.307 | 0.398 |
| NeoRez and Tospearl | After | 0.374 | 0.429 | 0.428 | 0.449 |

As can be seen from the results, chlorination does not significantly affect the performance of the coating layers containing silicone-modified polyurethanes and silicone particles tested. Accordingly, articles containing the coating layer according to the invention substantially retain the reduced friction and lubricity properties through the chlorination process.

Industrial Applicability

The invention can be used in a variety of elastomeric articles which contain a contacting surface, e.g., a skin-contacting surface, and in which ease of donning or lubricity are desirable attributes for their function. Examples of such articles include, but are not limited to, partial gloves such as finger coverings, bandages, dental gloves, ureters, catheters, condoms, sheaths and sheath-like articles such as incontinence devices, protective sheaths or covers, and the like.

The complete disclosures of all patents, patent applications, and publications are incorporated herein by reference as if each were individually incorporated by reference. The invention has been described with reference to various specific and preferred embodiments and techniques. However, it should be understood that many variations and modifications may be made while remaining within the spirit and scope of the invention.

What is claimed is:

1. An elastomeric article having an elastomeric material and a coating layer adhered to said elastomeric material, which coating layer comprises:
   a) a silicone-functionalized polymer; and
   b) silicone particles integrated throughout said polymer; wherein the coating layer is on a contacting surface of the article and there is a chemical affinity between the silicone functional groups on both the polymer and the silicone particles.

2. The elastomeric article according to claim 1 wherein the article is a glove.

3. The elastomeric article according to claim 2 wherein the glove is a surgical glove.

4. The elastomeric article according to claim 3 wherein the glove is a powder-free surgical glove.

5. The elastomeric article according to claim 1 wherein the elastomeric material is a natural or synthetic polymer.

6. The elastomeric article according to claim 5 wherein the elastomeric material is a natural rubber.

7. The elastomeric article according to claim 1 wherein the silicone-modified polymer is selected from the group consisting essentially of polyurethane, acrylic, vinyl, alkyl, ester and EPDM, and combinations thereof.

8. The elastomeric article according to claim 7 wherein the silicone-modified polymer is a polyurethane.

9. The elastomeric article according to claim 1 wherein the silicone particles comprise siloxane bonds.

10. The elastomeric article according to claim 9 wherein the silicone particles have a particle size ranging from about 0.1 microns to about 15.0 microns.

11. The elastomeric article according to claim 10 wherein the silicone particles have a particle size ranging from about 0.1 microns to about 12.0 microns.

12. The elastomeric article according to claim 11 wherein the silicone particles have a particle size ranging from about 0.2 microns to about 0.8 microns.

13. The elastomeric article according to claim 12 wherein the silicone particles comprise siloxane bonded alkyl groups.

14. The elastomeric article according to claim 1 wherein the polymer to particle ratio is from about 10 to 1 to about 1 to 1.

15. The elastomeric article according to claim 14 wherein the polymer to particle ratio is about 3 to 1.

16. The elastomeric article according to claim 1 wherein the contacting surface has a coefficient of friction of less than about 0.6.

17. The elastomeric article of claim 15 wherein the contacting surface has a coefficient of friction of less than 0.5.

18. An aqueous dispersion for coating elastomeric materials to increase lubricity comprising:
   a) a silicone-functionalized polymer; and
   b) silicone particles;
      wherein there is a chemical affinity between the silicone functional groups on both the polymer and the silicone particles.

19. The dispersion according to claim 18 wherein said silicone-modified polymer is a polymer selected from the group consisting essentially of polyurethane, acrylic, vinyl, alkyl, ester, and EPDM, and combinations thereof.

20. The dispersion according to claim 19 wherein the silicone-modified polymer is a silicone-modified polyurethane.

21. The dispersion according to claim 18 wherein the silicone particles comprise siloxane bonds.

22. The dispersion according to claim 18 wherein the silicone particles have a particle diameter size ranging from about 0.1 microns to about 15.0 microns.

23. The dispersion according to claim 22 wherein the silicone particles have a particle diameter size ranging from about 0.1 microns to about 12.0 microns.

24. The dispersion according to claim 23 wherein the silicone particles have a particle diameter size ranging from about 0.2 microns to about 0.8 microns.

25. The dispersion according to claim 24 wherein the silicone particle comprises siloxane bonded alkyl groups.

26. The dispersion according to claim 18 further comprising surfactants, lubricants, defoamers, and curing agents.

27. A method of making an elastomeric article comprising the steps of:
   a) forming a first layer of elastomeric material; and
   b) adhering a second, friction-reducing coating layer to the first layer, said coating layer being formed from a dispersion comprising a silicone-functionalized polymer in combination with silicone particles integrated therein, wherein there is a chemical affinity between the silicone functional groups on both the polymer and the silicone particles.

28. The method according to claim 27 wherein the elastomeric article is a glove.

29. The method according to claim 27 wherein the elastomeric material is a natural or synthetic polymer.

30. The method according to claim 29 wherein then elastomeric material is a natural rubber.

31. The method according to claim 27 wherein the silicone-modified polymer is a polymer selected from the group consisting essentially of polyurethane, acrylic, vinyl, alkyl, ester and EPDM, and combinations thereof.

32. The method according to claim 31, wherein the silicone-modified polymer is a silicone-modified polyurethane.

33. The method according to claim 27 wherein the silicone particles contain siloxane bonds.

34. The method according to claim 33 wherein the silicone particles have a particle diameter size ranging from about 0.1 microns to about 15.0 microns.

35. The method according to claim 34 wherein the silicone particles have a particle diameter size ranging from about 0.1 microns to about 12.0 microns.

36. The method according to claim 35 wherein the silicone particles have a particle diameter size ranging from about 0.2 microns to about 0.8 microns.

37. The method according to claim 36 wherein the silicone particle comprises siloxane bonded alkyl groups.

38. The method according to claim 27 further comprising:
   c) subjecting the coated elastomeric article to a chlorination process;
      wherein said elastomeric article is a powder-free article.

39. A method of making a powder-free glove comprising the steps of:
   a) forming a first layer of elastomeric material;
   b) adhering a second, friction-reducing coating layer to said first layer, said coating layer being formed from a dispersion containing a silicone-functionalized polymer in combination with silicone particles integrated therein wherein there is a chemical affinity between the silicone functional groups on both the polymer and the silicone particles; and
   c) subjecting the coated glove to a chlorination process.

* * * * *